US012557797B2

(12) United States Patent
Unger et al.

(10) Patent No.: US 12,557,797 B2
(45) Date of Patent: Feb. 24, 2026

(54) PACKAGE FOR PRE-DOSED UNITS FOR INSECT FARMING

(71) Applicant: Livin Farms AgriFood GmbH, Vienna (AT)

(72) Inventors: Katharina Unger, Vienna (AT); Jürgen Wixler, Dissen am Teutoburger Wald (DE)

(73) Assignee: Livin Farms AgriFood GmbH, Vienna (AT)

( * ) Notice: Subject to any disclaimer, the term of this patent is extended or adjusted under 35 U.S.C. 154(b) by 0 days.

(21) Appl. No.: 18/883,208

(22) Filed: Sep. 12, 2024

(65) Prior Publication Data

US 2025/0081948 A1     Mar. 13, 2025

(51) Int. Cl.
A01K 67/30          (2025.01)

(52) U.S. Cl.
CPC ........ A01K 67/30 (2025.01); *A01K 2227/706* (2013.01)

(58) Field of Classification Search
CPC .......................... A01K 67/30; A01K 2227/706
See application file for complete search history.

(56) References Cited

U.S. PATENT DOCUMENTS 3,006,106 A * 10/1961 Shuler ..................... A01K 97/04
                                                        43/4
4,055,911 A * 11/1977 Aylor ...................... A01K 97/04
                                                        119/6.7

4,172,336 A * 10/1979 Aylor ..................... A01K 97/04
                                                        119/6.7
10,448,623 B1 * 10/2019 Selby ..................... A01K 67/30
11,291,190 B1 * 4/2022 Peeters ................ A01K 29/005
11,490,604 B2 * 11/2022 Massaro ................ A01K 67/30
11,570,972 B2 * 2/2023 Comparat .............. A01K 67/30
11,723,349 B2 * 8/2023 Lepek ................ G06F 18/2431
                                                        119/6.5
11,730,152 B1 * 8/2023 Freeman .............. B07C 5/3427
                                                        382/110
11,950,579 B2 * 4/2024 Lepek ................... A01M 1/223
(Continued)

FOREIGN PATENT DOCUMENTS

CN          115968837          4/2023
WO          2022/048792        3/2022
(Continued)

OTHER PUBLICATIONS

Google Translation of WO2022232891 (Year: 2022).*
Europe Search Report/Office Action (EP SR/OA) conducted in counterpart Europe Appln. No. 23197145.8 (Mar. 7, 2024).

*Primary Examiner* — Monica L Perry
*Assistant Examiner* — Aaron M Rodziwicz
(74) *Attorney, Agent, or Firm* — GREENBLUM & BERNSTEIN, P.L.C.

(57) ABSTRACT

A package, method and arrangement for insect farming. The package is filled with a predetermined quantity of insects, and includes a package body; and a package closure configured to close the package body to prevent the insects from escaping from the package. The closed package body is configured to open at least partially under at least one of: at least one predetermined environmental condition, or in an event of consumption by the insects in the package body in order to release the insects.

14 Claims, 2 Drawing Sheets

(56)                    References Cited

U.S. PATENT DOCUMENTS

| | | | | |
|---|---|---|---|---|
| 2003/0188698 | A1* | 10/2003 | Donaldson ............. | A01K 67/30 |
| | | | | 119/678 |
| 2015/0013609 | A1* | 1/2015 | Weder .................... | A01K 67/30 |
| | | | | 119/6.5 |
| 2016/0066552 | A1* | 3/2016 | Arsiwalla .............. | A01K 67/33 |
| | | | | 119/6.5 |
| 2018/0070566 | A1* | 3/2018 | Comparat .............. | A01K 67/30 |
| 2022/0217957 | A1* | 7/2022 | Baptistan ............... | A01K 67/30 |
| 2023/0363363 | A1* | 11/2023 | Lepek .................... | A01K 67/30 |
| 2024/0008448 | A1* | 1/2024 | Gelder ................... | G01G 17/08 |
| 2024/0032518 | A1* | 2/2024 | Slade .................... | A01K 67/30 |

FOREIGN PATENT DOCUMENTS

| | | |
|---|---|---|
| WO | 2022/144197 | 7/2022 |
| WO | 2022/232891 | 11/2022 |

* cited by examiner

PACKAGE FOR PRE-DOSED UNITS FOR INSECT FARMING

CROSS-REFERENCE TO RELATED APPLICATION

This application claims priority under 35 U.S.C. § 119(a) to Europe Application No. 23197145.8 filed Sep. 13, 2023, the disclosure of which is expressly incorporated by reference herein in its entirety.

BACKGROUND

1. Field of the Invention

The present invention relates to a package filled with a predetermined quantity of insects, wherein the insects are in a same specific growth stage, in particular as larvae, or in different specific growth stages, wherein the package is closed to prevent the insects from escaping from the package. The present invention further relates to a use and an arrangement of the package.

2. Discussion of Background Information

An insect's life cycle includes several growth stages (e.g., egg, larva, pupa, and adult insect), with the duration of these growth stages varying depending on the species of insect. The term "insect" comprises the insect in its various growth stages. Depending on the type of insect, the growth phases can take a few days to a few weeks. In industrial insect farming, insects are bred in particular for food and animal feed. From the production of insect eggs to the rearing of adult insects, industrial insect farming covers the various growth stages of insects. After the insects hatch from the eggs as larvae, they are usually stored in containers or boxes filled with substrate in predetermined environmental conditions, where they grow into adult insects.

During storage in the containers, the larvae can also pupate into pupae, from which the adult insects grow. The substrate comprises food for the larvae. The adult insects are "harvested," i.e., removed from the containers, and can then be further processed, e.g., into protein-rich end products such as oil or powder. Similar to other industries, production facilities in industrial insect farming are also largely automated.

Layouts of such production facilities are disclosed in WO 2022/144197 A1, in US 2018/0070566 A1 or in CN 115968837 A. In various stations, the insects are first placed as larvae in containers filled with substrate, then the containers are stored and after a certain growth period they are removed again and emptied if necessary (e.g., when the insects have grown from larvae into adult insects). The insects as larvae can either be filled into the containers together with the substrate or separately. The containers can also be removed at predetermined intervals and then stored again, for example after an inspection or after adding more substrate. In US 2016/0066552 A1, the contents of the containers are controlled by cameras, wherein a dosing device serves to fill additional substrate into the containers. This removal and storage increases the effort required during insect farming.

To fill the containers with insects as larvae and/or the substrate, dosing devices are usually provided that comprise a weighing device. The weighing device is used to check, after filling, whether a predetermined quantity (dosage) of larvae and/or substrate is present in the relevant container.

WO 2022/144197 A1 or WO 2022/048792 A1 discloses a dosing device, wherein weighing is used to check whether there are enough larvae and/or enough substrate in the containers. In addition to the increased effort required by the weighing device, weighing also slows down production.

In principle, the quantity of insects as larvae depends on the substrate in the container. The substrate has properties such as amount, density, humidity, nutrient content, etc. Depending on which substrate with which properties is present in the container, a corresponding quantity of larvae must be dosed in order to obtain, for example, a predetermined density of the larvae (number of larvae per unit volume) and the substrate in the container in order to achieve the best possible yield in insect farming. Of course, this density also depends on the container volume. The density of the larvae and the substrate in the container influences the growth of the insects. For this purpose, there is a known connection between the substrate in the container and the density of insects in the container to ensure the best possible farming success.

SUMMARY

Embodiments improve insect farming, in particular, to increase the accuracy of the dosage of the insects in the container, for example depending on a substrate in the container, and thus to improve the growth of the insects in the container and the farming success.

According to embodiments, a package is designed to open at least partially under at least one predetermined environmental condition and/or by consumption by the insects in the package in order to release the insects. On the one hand, the package allows for precise dosing of the insects onto a predetermined substrate when used in a container, thus allowing for optimal growth of the insects. On the other hand, additional work steps, such as opening the package, are eliminated.

In a preferred embodiment, the at least one predetermined environmental condition is a temperature and/or an air humidity and/or a humidity and/or the presence of a gaseous or liquid medium at the location of use of the package. For example, when the package is used in a container, it is easily possible for the predetermined substrate and its properties, such as humidity, to cause the package in the container to open (itself) at least partially, allowing the insects to leave the package through the resulting opening. Alternatively, the package in the container can be sprayed with water, for example, so that the package opens at least partially.

Advantageously, the at least one predetermined environmental condition triggers a chemical reaction with a material of the package that at least partially dissolves or decomposes the package for opening. The package can be exposed to water (e.g., by spraying the package), for example when used in a container, wherein the water reacts with the material of the package and the package partially opens and the insects in the package are released. It is particularly advantageous if the package dissolves or decomposes completely as a result of the chemical reaction, thereby reducing waste from insect farming.

In an advantageous embodiment, the package is at least partially permeable to air in order to ensure the survival of the insects in the package, preferably for a predetermined period of time. This ensures that the insects are prevented from escaping from the package, while the insects are provided with sufficient air in the package for several days or weeks.

In a further preferred embodiment, the package is airtight, wherein a predetermined amount of air is present in the package to ensure survival of the insects in the package, preferably for a predetermined period of time. This is particularly advantageous because the package may be compressed to an unacceptable extent during transport or storage of the package. This can cause harm to the insects. However, since the predetermined amount of air cannot escape from the package, the package forms a kind of air cushion, which prevents the package from being compressed and thus protects the insects.

Advantageously, the package is also filled with a substrate, wherein the substrate has predetermined properties to ensure the survival of the insects in the package, preferably for a predetermined period of time. This makes it easy to ensure that the insects are sufficiently supplied with humidity, nutrients, etc. even during transport or storage over several days or weeks and thus survive, for example, until they are used in insect farming.

When advantageously using the package in insect farming, the package is placed in a container for insect farming, wherein the at least one predetermined environmental condition is present in the container and/or the insects in the package consume the package in order to release the insects in the package into the container in order to obtain a predetermined density of insects in the container. The package allows for easy handling and dosing of the insects in insect farming, thereby promoting optimal growth of the insects.

In a further advantageous use of the package in insect farming, the package is additionally opened at least partially mechanically in order to release the insects in the package into the container. As a result, for example, at least one opening can be created from which the package opens further due to the at least one predetermined environmental condition and/or due to consumption by the insects. This can shorten the time until the insects can leave the package because at least one opening is already present.

In the advantageous arrangement of a package in a container filled with substrate for insect farming, at least one predetermined environmental condition is present in the container in order to at least partially open the package and to release the larvae into the substrate. Thus, the package can easily be brought into contact with the substrate, which for example has a predetermined humidity, whereby the package opens (itself) at least partially.

Embodiments are directed to a package filled with a predetermined quantity of insects that includes a package body; and a package closure configured to close the package body to prevent the insects from escaping from the package. The closed package body is configured to open at least partially under at least one of: at least one predetermined environmental condition, or in an event of consumption by the insects in the package body in order to release the insects.

In embodiments, the insects can be in a specific growth stage, and the specific growth stage may be as larvae.

In other embodiments, the insects may be in different specific growth stages.

According to embodiments, the at least one predetermined environmental condition can be at least one of: a temperature, an air humidity, a humidity, or a presence of a gaseous or liquid medium at a location at which the package is to be used.

In accordance with embodiments, the at least one predetermined environmental condition may trigger a chemical reaction with at least a material of the package body that creates an opening in the package body by at least partially dissolving or decomposing the package body.

In accordance with other embodiments, at least the package body is at least partially permeable to air in order to ensure the survival of the insects in the package. The at least partially permeable to air package is configured to ensure the survival of the insects in the package for a predetermined period of time.

According to other embodiments, the package body can be airtight and a predetermined amount of air may be contained in the closed package body to ensure the survival of the insects in the package. The predetermined amount of air in the closed airtight package body can ensure the survival of the insects in the package for a predetermined period of time.

In other embodiments, the package body can be additionally filled with a substrate. The substrate has predetermined properties.

Embodiments are directed to a method for insect farming using the above-described package. The method includes placing the package containing the insects in a container for insect farming, releasing the insects from the package by at least one of: providing the at least one predetermined environmental condition in the container, or the insects in the package consuming the package, whereby in order to release the insects in the package into the container in order to obtain a predetermined density of insects is released in the container.

In accordance with still further embodiments, the method may further include at least partially mechanically opening the package to release the insects in the package into the container.

Embodiments are directed to an arrangement of the above-described package in a container filled with substrate for insect farming. The at least one predetermined environmental condition is present in the container in order to at least partially open the package and to release the insects in the package into the substrate in the container.

Other exemplary embodiments and advantages of the present invention may be ascertained by reviewing the present disclosure and the accompanying drawing.

BRIEF DESCRIPTION OF THE DRAWINGS

The present invention is described in greater detail below with reference to FIG. 1 to 4, which show schematic and non-limiting advantageous embodiments of the invention by way of example. In the figures.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
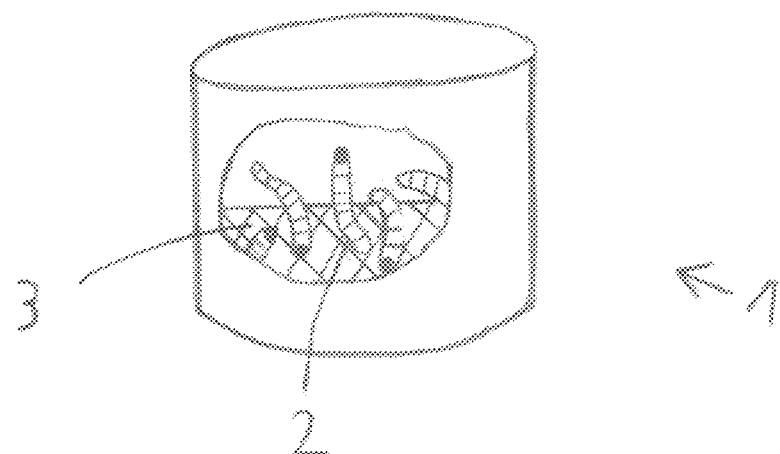
FIG. 1 shows the basic structure of the package according to the invention.

FIG. 1 shows the basic structure of the package 1 according to the invention for insect farming, wherein the package 1 is shown partially broken open merely for illustration purposes to provide a view into the package 1.

The package 1 is filled with a predetermined quantity of insects 2, wherein the insects are in a specific growth stage. In this case, the insects 2 can all be in the same growth stage, in particular as larvae (as shown in FIG. 1) or as eggs, pupae, etc., or they may be in different specific growth stages. In this case, the insects 2 can in particular comprise those species of insects 2 that are suitable for insect farming (e.g., larvae of a black soldier fly). The predetermined quantity of insects 2 can, for example, be between 1 g and 10 g.

The package 1 is closed to prevent the insects 2 from escaping from the package 1. The package 1 thus serves as a transport unit to allow a particular predetermined quantity of insects 2 in a specific growth stage to be transported in a packaged manner. This makes handling the insects 2 significantly easier, in particular when used in insect farming.

In FIG. 1, the package 1 is shown by way of example with a cylindrically shape (e.g., a cup) package body. Of course, the shape of the package body of package 1 is not limited thereto. In particular, cylindrical, square, or rectangular package bodies for packages 1 can be advantageous for transporting and/or storing a plurality of packages 1 in a space-saving manner.

Examples of further possible embodiments of the package 1 include bags, boxes, etc. The package 1 can also be divided into package units, e.g., a cup having a plurality of chambers in which the insects 2 are filled. The density of the insects 2 in the package 1 naturally depends on the volume of the package 1 and on the quantity of insects 2 in the package 1.

A separate part of the package 1, such as a lid, screw cap, etc., can be used as a package closure to close the package 1. It is also possible that this package closure is not a separate part provided for closing, but can be, for example a closure by gluing, (heat) sealing, etc. The package 1 can therefore also be closed by a variety of package closures, for example by gluing, sealing, closing a lid, etc.

Figure 2:
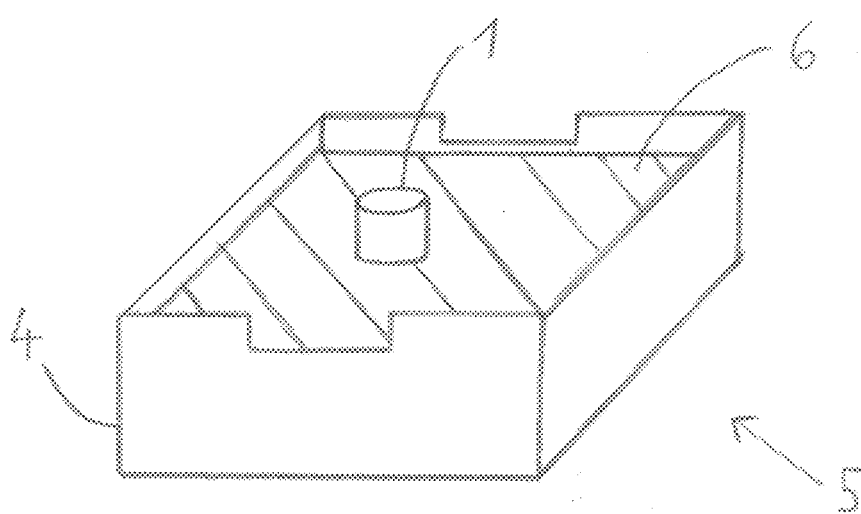
FIG. 2 shows an arrangement of the package in a container.
Figure 3:
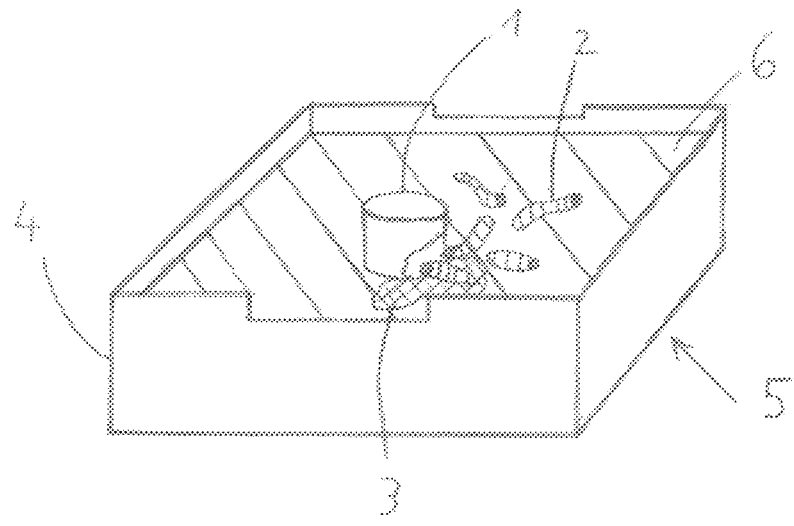
FIG. 3 shows the package in the container, partially opened.
Figure 4:
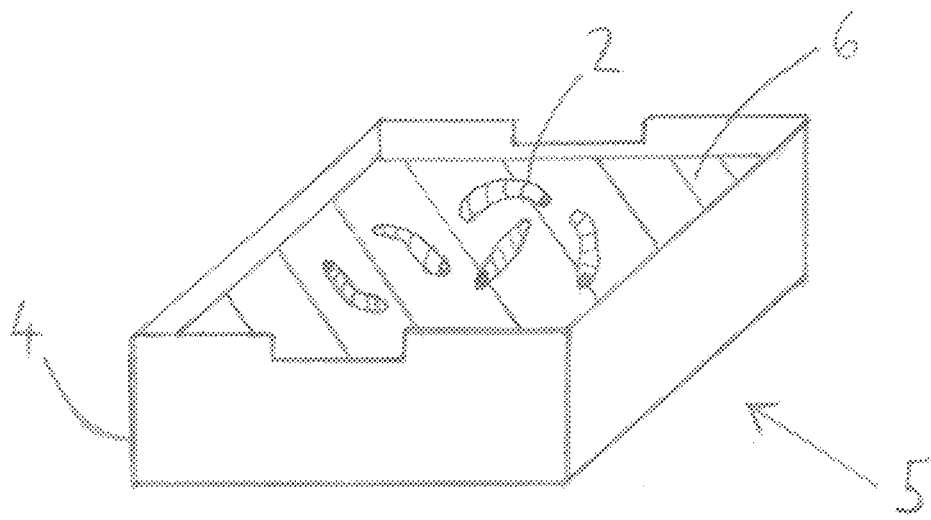
FIG. 4 shows the insects in the substrate of the container.

The package 1 is designed to open at least partially under at least one predetermined environmental condition and/or in the event of consumption by the insects 2 in the package 1 in order to release the insects 2. In this case, the package 1 itself includes or may consist of at least one material, and the at least one predetermined environmental condition triggers, for example, a chemical reaction with the at least one material of the package 1 that can open the package by at least partially dissolving or decomposing at least a part of the package 1. The package 1 can, for example, be designed to be biodegradable, for example made of a biodegradable plastic or paper or cardboard. The at least one predetermined environmental condition is preferably a temperature and/or an air humidity and/or a humidity and/or the presence of a gaseous or liquid medium at the location of use of the package 1. For example, contact with water and/or with a substrate 6, e.g., in a container 4 (as shown in FIGS. 2-4), may result in at least partial degradation, decomposition, or dissolution of the package 1, whereby the package 1 opens at least partially and the insects 2 are released.

For example, a substrate 6 in which the insects 2 are to be bred can have a predetermined humidity or temperature that leads to at least partial degradation, decomposition, or dissolution of the package 1. The predetermined environmental conditions that must be present depend on the material of the package 1, but can be assumed to be known.

Furthermore, the at least one predetermined environmental condition can be present in the package 1 itself (e.g., air with a predetermined humidity and/or temperature). However, the package 1 is designed in such a way that the package 1 remains closed during the time from filling to use.

The at least one material of the package 1 can be alternatively or additionally formed to be consumed by the insects 2 in the package 1. In this case too, the package 1 is designed in such a way that the package 1 remains closed during the time from filling to use.

Examples of the at least one material of the package 1 are filter paper, edible paper, dough material (e.g., made of rice, sugar, etc.), polyvinyl acetate (PVA), plastic (e.g., biodegradable), etc. Depending on the type of material, the package 1 can be elastic (deformable) or rigid (non-deformable). It is also conceivable that the package 1 is made of different materials.

The time it takes for the package 1 to at least partially open under the at least one predetermined environmental condition and/or due to consumption by the insects 2 depends on the material, the wall thickness of the material, etc. For example, the package 1 can be designed with different wall thicknesses of the material, whereby points are formed on the package 1 that open faster than the rest of the package 1 (i.e., a kind of "target opening points").

The package 1 is closed before use in insect farming to prevent the insects 2 from escaping from the package 1. For example, the package 1 can be closed by gluing, welding, etc., wherein the way in which the package 1 is closed can depend on the material used. It is also conceivable to close the package 1, e.g., as shown in FIG. 1, as a cup, with a lid that adheres to the package 1 by friction. Of course, this lid can also be glued or welded.

The package 1 is preferably at least partially permeable to air in order to ensure the survival of the insects 2 in the package 1, preferably for a predetermined period of time. If the transport and/or storage of the package 1 extends over several days or weeks, it is thus ensured that the insects 2 are sufficiently supplied with air. For this reason, the package 1 can, for example, have an opening that is configured to allow air to pass into the package 1 but prevents the insects 2 from escaping from the package 1. In another embodiment, the package 1 is airtight, wherein a predetermined amount of air is present in the package 1 to ensure the survival of the insects 2 in the package 1, preferably for a predetermined period of time. Because the amount of air cannot escape, the package 1 forms a kind of air cushion. Thus, the insects 2 can be protected during transport and/or during storage of the package 1, e.g., against compression of the package 1 by external influences. The predetermined amount of air in the package 1 can be created, for example, during the production of the package 1.

As shown in FIG. 1, the package 1 is preferably also filled with a substrate 3, wherein the substrate 3 has predetermined properties to ensure the survival of the insects 2 in the package 1, preferably for a predetermined period of time. The substrate 3 creates conditions for the insects 2 in the package 1 (e.g., sufficient humidity, food, nutrients, etc.) so that the insects 2 can survive even during transport and/or storage of the package 1 for several days or weeks. Gelatin, agartine (agar-agar), cereal mixtures, or the like are suitable as a substrate 3 for this purpose. In particular, the quantity of insects 2 in the package 1 and the properties of the substrate 3, such as the amount, density, humidity, nutrient content, etc., are coordinated with one another.

In principle, depending on how the package 1 is configured (e.g., material, volume, properties of the substrate 3, etc.) and which environmental conditions are present (e.g., temperature, humidity, etc.), the growth of the insects 2 in the package 1 can be influenced during transport and/or storage. In addition, it can be prevented, for example by a predetermined maximum period of time of transport and/or storage as well as by predetermined environmental conditions, that the insects 2 in the package 1 consume the package 1 before use in insect farming and thereby open it.

FIG. 2 shows a preferred arrangement 5 of the package 1 in a container 4 filled with substrate 6 for insect farming. In the container 4, the at least one predetermined environmental condition for at least partially opening the package 1 (as shown in FIG. 3) is present so that the insects 2 can get out of the package 1 into the substrate 6 in the container 4. The predetermined environmental condition can be set, for example, in an insect farming facility. The substrate 6 in the container 4 can have similar properties to the substrate 3 in the package 1. The at least one predetermined environmental condition can, for example, describe a property of the substrate 6 in the container 4, such as humidity. It is also possible that the package 1 in the container 4 is sprayed with water or that a certain humidity and temperature is set. During use, the package 1 can additionally be at least partially opened mechanically (e.g., by cutting or punching) in order to release the insects 2 in the package 1 into the container 4.

In FIG. 3, the package 1 is shown at least partially opened, wherein the insects 2 have left the package 1 and entered the substrate 6 in the container 4. In this case, the substrate 3 from the package 1 has also passed into the substrate 6 in the container 4. If the package 1 remains in the container 4 for a certain period of time, it can create local environmental conditions in the container 4 (a kind of microclimate). Thus, the insects 2 can remain in the package 1 to be protected until the package 1 has completely dissolved and/or been consumed by the insects 2. The local environmental conditions may be favorable for better growth of the insects 2 in the container 4, thereby increasing the efficiency of insect farming. The substrate 3 can, for example, be consumed by the insects 2 and/or mix with the substrate 6 in the container 4.

In FIG. 4, the insects 2 have spread throughout the substrate 6 of the container 4, wherein the package 1 has completely dissolved and/or been consumed by the insects 2. This eliminates the need to remove the package 1 from the container 4. The substrate 3, for example, was consumed by the insects 2 and is therefore no longer shown in FIG. 4.

Due to the predetermined quantity of insects 2 in the package 1, there is now a predetermined density of the insects 2 in the substrate 6 in the container 4. However, the package 1 does not necessarily have to dissolve completely. It is quite possible that residues of the package 1 remain in the container 4 and that these residues are removed at a later time.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A method for insect farming using a package having a package body filled with a predetermined quantity of insects; and a package closure configured to close the package body to prevent the insects from escaping from the package, wherein an opening through which the insects are released from the package is formed in the closed package body under at least one of: at least one predetermined environmental condition, or in an event of consumption of a part of the closed package body by the insects in the package, the method comprising:
    placing the package containing the insects in a container for insect farming; and
    releasing the insects from the package by at least one of:
        exposing the package to the at least one predetermined environmental condition provided in the container, or
        the insects in the package consuming a part of the package body,
    whereby the insects in the package are released into the container in order to obtain a predetermined density of insects in the container.

2. The method according to claim 1, wherein the insects in the package are in a specific growth stage.

3. The method according to claim 2, wherein the specific growth stage is as larvae.

4. The method according to claim 1, wherein the insects are in different specific growth stages.

5. The method according to claim 1, wherein the at least one predetermined environmental condition in the container is at least one of:
    a temperature,
    an air humidity,
    a humidity, or
    a presence of a gaseous or liquid medium
at a location at which the package is to be used.

6. The method according to claim 1, wherein the at least one predetermined environmental condition triggers a chemical reaction with at least a material of the package body that creates the opening in the package body by dissolving or decomposing a part the package body.

7. The method according to claim 1, wherein at least a part of the package body is permeable to air in order to ensure the survival of the insects in the package.

8. The method according to claim 7, wherein the part of the package permeable to air is configured to ensure the survival of the insects in the package for a predetermined period of time.

9. The method according to claim 1, wherein the package body is airtight and a predetermined amount of air is contained in the closed package body to ensure the survival of the insects in the package.

10. The method according to claim 9, wherein the predetermined amount of air in the closed airtight package body ensures the survival of the insects in the package for a predetermined period of time.

11. The method according to claim 1, wherein the package body is additionally filled with a substrate.

12. The method according to claim 11, wherein the substrate has predetermined properties.

13. The method according to claim 1, wherein the releasing the insects from the package further mechanically opening a part of the package to release the insects in the package into the container.

14. An arrangement for insect farming comprising:

a package having a package body filled with a predetermined quantity of insects and a package closure configured to close the package body to prevent the insects from escaping from the package, wherein an opening through which the insects are released from the package is formed in the closed package body under at least one of: at least one predetermined environmental condition, or in an event of consumption of a part of the closed package body by the insects in the package;

a container filled with substrate for insect farming, wherein the package is provided in the container and the at least one predetermined environmental condition is present in the container in order to form the opening in the closed package body and release the insects in the package into the substrate in the container.

* * * * *